United States Patent [19]

Jaksch

[11] Patent Number: 5,200,551

[45] Date of Patent: Apr. 6, 1993

[54] METHOD OF PREPARING AN INTERMEDIATE FOR THE MANUFACTURE OF BAMBUTEROL

[75] Inventor: Peter Jaksch, Järna, Sweden

[73] Assignee: Aktiebolaget Astra, Sodertalje, Sweden

[21] Appl. No.: 741,424

[22] PCT Filed: Nov. 20, 1990

[86] PCT No.: PCT/SE90/00792

§ 371 Date: Jul. 31, 1991

§ 102(e) Date: Jul. 31, 1991

[87] PCT Pub. No.: WO91/08197

PCT Pub. Date: Jun. 13, 1991

[30] Foreign Application Priority Data

Dec. 1, 1989 [SE] Sweden ............... 8904064

[51] Int. Cl.$^5$ ............... C07C 269/00
[52] U.S. Cl. ............... 560/132; 562/555
[58] Field of Search ............... 560/132, 25

[56] References Cited

U.S. PATENT DOCUMENTS 3,404,975 10/1968 Wilson et al. ............... 560/29 X
4,419,364 12/1983 Olsson et al. ............... 560/136 X
4,451,663 5/1984 Olsson et al. ............... 560/29
4,925,971 5/1990 Aoki et al. ............... 560/137

FOREIGN PATENT DOCUMENTS 3441108 5/1986 Fed. Rep. of Germany.

*Primary Examiner*—Jose G. Dees
*Assistant Examiner*—Vera C. Clarke
*Attorney, Agent, or Firm*—White & Case

[57] ABSTRACT

The present invention relates to an improved method for the preparation of an intermediate for bambuterol, i.e. for the preparation of 2'-bromo-3,5-di[N,N-dimethylcarbamoyloxy]acetophenone (1), by reacting 3,5-dihydroxyacetophenone with N,N-dimethylcarbamoylchloride in ethyl acetate, isopropylacetate, butylacetate, ethylmethylketone or isobutylmethylketone as a solvent with small amount of pyridine as a catalyst and using crystallized potassium carbonate as a base, quenching with water, removing the solvent and dissolving of the resulting 3,5-di[N,N-dimethylcarbamoyloxy]acetophenone in ethyl acetate, to which dissolved hydrogen bromide is added and then bromine, whereupon the resulting intermediate (1) is collected in the form of crystals.

2 Claims, No Drawings

METHOD OF PREPARING AN INTERMEDIATE FOR THE MANUFACTURE OF BAMBUTEROL

The present invention relates to an improved method for the preparation of the intermediate for bambuterol, i.e. for the preparation of the 2'-bromo-3,5-di[N,N-dimethyl-carbomoyloxy]acetophenone, having the formula

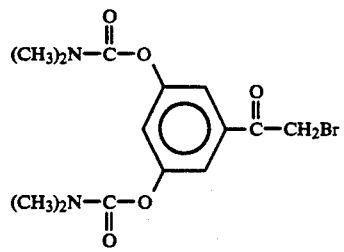

In U.S. Pat No.4,451,663 a method of manufacturing the intermediate 2'-bromo-3,5-di[N,N-dimethylcarbamoyloxy]acetophenone of the formula (1) is disclosed, called route A2 therein, according to which 3,5-dihydroxyacetophenone, having the formula

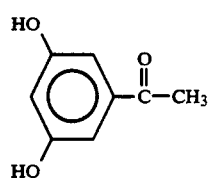

is reacted with N,N-dimethylcarbamoylchloride (DMCC) having the formula

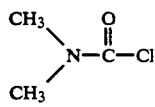

using pyridine as solvent and base for the uptake of hydrochloric acid formed during the reaction. The resulting compound, 3,5-di[N,N-dimethylcarbamoyloxy]acetophenone having the formula

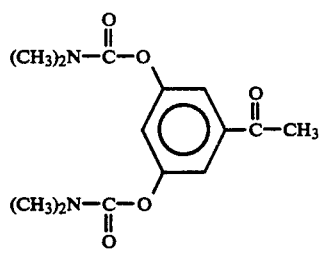

is not isolated but further reacted with bromine in dioxan solvent resulting in the formation of 2'-bromo-3,5-di[N,N-dimethylcarbamoyloxy]acetophenone (1).

There is a great desire to avoid working with pyridine as a solvent. One method was tested in order to avoid using pyridine as a solvent, according to which the reaction was performed in methylene chloride with potassium carbonate as a base with catalytical amount of pyridine present. The drawbacks with the process was a long reaction time for N,N-dimethylcarbamoylchloride (DMCC), >24 hours, and a long quenching time for DMCC, >24 hours, and separation problems in the work-up step (emulsion and small density difference). Methylene chloride is not a preferred solvent either, because of its toxicity.

The object of the invention is to provide an improved method for the preparation of the intermediate 2'-bromo-3,5-di -[N,N-dimethylcarbamoyloxy]acetophenone (1) for the production of bambuterol avoiding the use of pyridine and methylene chloride as solvents and eliminating the separation problems in the work-up step.

This is attained according to the present invention by reacting 3,5-dihydroxyacetophenone

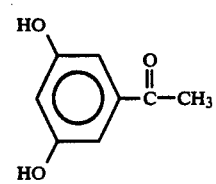

with N,N-dimethylcarbamoylchloride, $(CH_3)_2NCOCl$, in a solvent, quenching with water, removing the solvent and dissolving of the resulting 3,5-di-[N,N-dimethylcarbamoyloxy]acetophenone

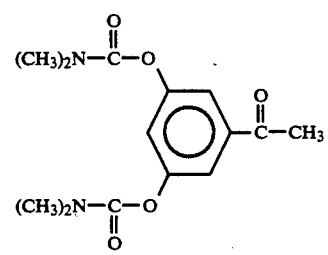

in ethyl acetate, to which is added dissolved hydrogen bromide and then bromine, whereupon the resulting intermediate (1) is collected in the form of crystals, wherein the reaction between said 3,5-dihydroxyacetophenone (2) and N,N-dimethylcarbamoylchloride (3) is carried out in ethylacetate, isopropylacetate, butylacetate, ethylmethylketone or isobutylmethylketone as the solvent with a small amount of pyridine as a catalyst using a base comprising crystallized potassium carbonate.

According to a preferred embodiment of the invention potassium carbonate having a crystal water content of 11–13% is used. This might be achieved by using a mixture of crystallized and calcinated potassium carbonate, resulting in a easily stirred two-phase system.

Calcinated potassium carbonate (completely dry) gives a slow and non-complete reaction, and the addition of water to the calcinated potassium carbonate results in a sticky mass which is difficult to stir. Further, free water should not be present in the reaction mixture because of the risk of hydrolysis of the reactants.

The bromination step which according to the invention first involves the addition of HBr, preferably dissolved in ethanol, and a second step charging with bromine, $Br_2$, has the advantage that the bromination will proceed calmly. When bromination is performed directly with bromine, the reaction will start very slowly and at a certain point it will proceed vigorously and will be hard to control.

The invention will now be described more in detail.

In the first step of the process the base, potassium carbonate, will take care of hydrochloric acid formed. According to the prior art process pyridine will act both as base and solvent. In the process according to the invention however, pyridine will only be present in catalytic amounts. Here the pyridine will initially take up the hydrochloric acid formed, which then will be transferred to the potassium carbonate, which is consumed.

Dry, that is calcinated, potassium carbonate, does not work very well as a base, and the reason is believed to be that it forms a separated phase which is non-miscible with the other phases. If calcinated potassium carbonate and water is used, the water will hydrolyze the N,N-dimethylcarbamoylchloride (DMCC).

According to the invention crystallized potassium carbonate is used as the base. The water will released slowly and the base will be slowly consumed by the hydrochloric acid, which is first taken up and then transferred from the catalytic amount of pyridine present in the reaction mixture.

The crystallized potassium carbonate contains about 1.5 moles of $H_2O$ which corresponds to about 16%. The optimum water content is 11–13%, and this content is obtained using a mixture of calcinated potassium carbonate and crystallized potassium carbonate.

The synthetic route is described more in detail below.

Flowsheet diagram of synthetic route

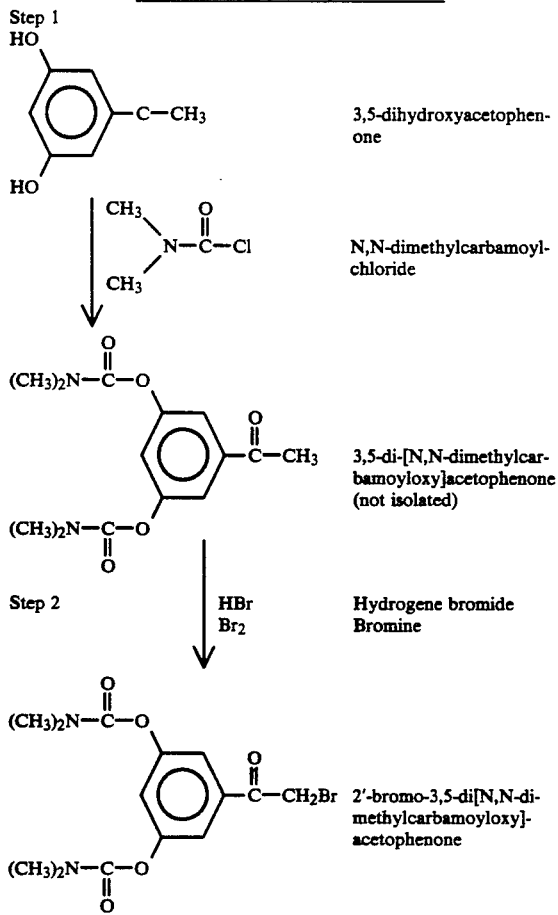

Step 1
HO — [structure] — C—CH3   3,5-dihydroxyacetophenone

CH3 N—C—Cl   N,N-dimethylcarbamoylchloride (CH3)2N—C—O— [structure] —C—CH3   3,5-di-[N,N-dimethylcarbamoyloxy]acetophenone (not isolated)

Step 2   HBr   Hydrogene bromide
         Br2   Bromine (CH3)2N—C—O— [structure] —C—CH2Br   2'-bromo-3,5-di[N,N-dimethylcarbamoyloxy]-acetophenone

STEP 1

Synthesis of
3,5-di-[N,N-dimethylcarbamoyloxy]acetophenone 500 liter scale

Chemicals

| | kg | molar weight | moles |
|---|---|---|---|
| In | | | |
| 3,5-dihydroxyacetophenone | 24.0 | 152.2 | 157.7 |
| Potassium carbonate × 1,5 $H_2O$* | 41.0 | 165.5 | 247.7 |
| Potassium carbonate calc. | 9.4 | 138.2 | 68.0 |
| Pyridine | 1.0 | 79.1 | 12.6 |
| Ethyl acetate | 136.0 | | |
| Dimethylcarbamoylchloride | 50.0 | 107.5 | 465.1 |
| Water | 180.0 | | |
| Sulphuric acid | ≈1.0 | | |
| Out | | | |
| 3,5-di-[N,N-dimethylcarbamoyloxy]acetophenone | | | |
| Yield calc. 95% | 44.1 | 294.3 | 149.8 |

*)The use of the hydrate form of potassium carbonate is essential for a successful reaction.

Procedure

Into a 500 liter enamelled reactor, connected to a scrubber containing ammonia/ethanol, is charged:
24 kg 3,5-dihydroxyacetophenone
41 kg potassium carbonate × 1,5 $H_2O$
9.4 kg potassium carbonate calcinated
96 kg (150 l) ethyl acetate
1.0 kg pyridine
50 kg dimethylcarbamoylchloride This mixture is stirred and heated to 70°±2° C., and after stirring for 2 hours at this temperature 120 kg water is charged at 70° C. and the mixture is stirred for 1,5 hours at 70°±2° C. After cooling to 20°–30° C. the reaction mixture is separated and the lower water phase is discarded.

To the organic phase is charged 60 kg water and pH is adjusted to 2–3 with about 1 kg sulphuric acid.

The phases are separated and the lower water phase is discarded. Ethyl acetate and water are removed by evaporation in the reactor at a jacket temperature of 60° C. and vacuum (<100 mbar). The evaporation residue is dissolved in 40 kg (50 l) ethyl acetate and is used directly in the bromination step.

STEP 2

Synthesis of
2'-bromo-3,5-di[N,N-dimethylcarbamoyloxy]acetophenone in laboratory scale

Chemicals

| | ml | g | molar weight | moles |
|---|---|---|---|---|
| In | | | | |
| 3,5-di-[N,N-dimethylcarbamoyloxy]acetophenone | | 21.8 | 294.3 | 0.074 |
| dissolved in ethyl acetate | 25 | 20.0 | | |
| Ethanol | 16 | 12.8 | | |
| Bromine | | 12.6 | 159.8 | 0.079 |
| Water | 36 | 36.0 | | |
| Ethanol | 15 | 12.0 | | |
| Hydrogen bromide compr. | | 3.2 | 80.9 | 0.040 |
| Out | | | | |
| 2'-bromo-3,5-di[N,N-dimethyl- | | | | |

| | ml | g | molar weight | moles |
|---|---|---|---|---|
| carbamoyloxy]acetophenone | | | | |
| Yield calc. 75% | | 20.7 | 373.2 | 0.055 |

Procedure

Into a 100 ml three necked flask is charged 21.8 g 3,5-di[N,N-dimethylcarbamoyloxy]acetophenone dissolved in ethylacetate and 3.2 g hydrogen bromide dissolved in 12.8 g (16 ml) ethanol.

At 12°±2° C. is charged 12.6 g bromine in 30–60 minutes.

After stirring for further 10 minutes at 12°±2° C. 36 ml (36 g) water is charged in about 15 minutes.

Thereafter the crystal slurry is cooled to −14°±2° C. and the crystals are collected on a filter and washed with 12 g (15 ml) cold (−14° C.) ethanol. The crystals are dried at 40° C. in vacuum.

The yield is about 20.7 g (75%).

I claim:

1. A method for the preparation of 2'-bromo-3,5-di-[N,N-dimethylcarbamoyloxy]acetophenone, having the formula

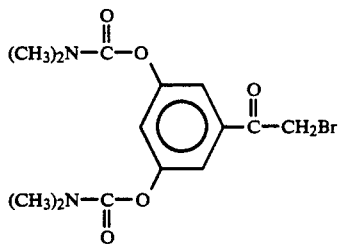

comprising: reacting 3,5-dihydroxyacetophenone

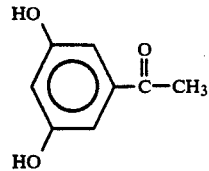

with N,N-dimethylcarbamoylchloride,

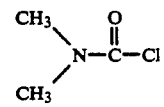

in a solvent, quenching with water, removing the solvent and dissolving of the resulting 3,5-di-[N,N-dimethylcarbamoyloxy]acetophenone

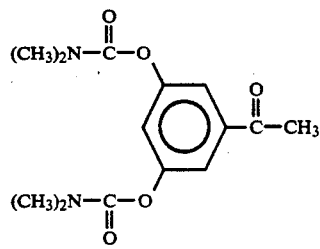

in ethyl acetate, to which dissolved hydrogen bromide is added and then bromine, whereupon the resulting intermediate (1) is collected in the form of crystals, wherein the reaction between said 3,5-dihydroxyacetophenone (2) and N,N -dimethylcarbamoylchloride (3) is carried out in ethylacetate, isopropylacetate, butylacetate, ethylmethylketone or isobutylmethylketone as the solvent with a small amount of pyridine as a catalyst using a base comprising crystallized potassium carbonate.

2. A method according to claim 1, wherein the base is in the form of a mixture of crystallized and calcinated carbonate having a total crystal water content of 11–13%.

* * * * *

UNITED STATES PATENT AND TRADEMARK OFFICE
CERTIFICATE OF CORRECTION

PATENT NO. : 5,200,551
DATED : April 6, 1993
INVENTOR(S) : Peter Jaksch

It is certified that error appears in the above-identified patent and that said Letters Patent is hereby corrected as shown below:

Title page, item [22], "Nov. 20, 1990" should read --Nov. 29, 1990--;

col. 1, line 6, the second "the" should read --an--;

col. 2, line 64, "Brt$_2$" should read --Br$_2$--;

col. 6, line 43, "calcinated" should be followed by --potassium--

Signed and Sealed this

Seventeenth Day of May, 1994

BRUCE LEHMAN

*Attest:*

*Attesting Officer*

*Commissioner of Patents and Trademarks*